(12) United States Patent
Liess et al.

(10) Patent No.: US 8,915,013 B2
(45) Date of Patent: Dec. 23, 2014

(54) METHOD FOR THE ERADICATION OF PATHOGENIC MICROORGANISMS IN AN AQUEOUS SYSTEM

(75) Inventors: Matthias Liess, Leipzig (DE); Sabine Duquesne, Leipzig (DE)

(73) Assignee: Helmholtz-Zentrum fur Umweltforschung GmbH, Leipzig (DE)

( * ) Notice: Subject to any disclaimer, the term of this patent is extended or adjusted under 35 U.S.C. 154(b) by 748 days.

(21) Appl. No.: 13/129,147

(22) PCT Filed: Nov. 12, 2009

(86) PCT No.: PCT/EP2009/065025
§ 371 (c)(1),
(2), (4) Date: Sep. 7, 2011

(87) PCT Pub. No.: WO2010/055080
PCT Pub. Date: May 20, 2010

(65) Prior Publication Data
US 2011/0308138 A1    Dec. 22, 2011

(30) Foreign Application Priority Data

Nov. 13, 2008 (DE) .................. 10 2008 043 715

(51) Int. Cl.
*A01M 1/20* (2006.01)
*A01N 63/00* (2006.01)

(52) U.S. Cl.
CPC .................................... *A01N 63/00* (2013.01)
USPC ............................................ 43/132.1; 43/124

(58) Field of Classification Search
CPC ... A01M 1/20; A01M 1/2016; A01M 1/2022; A01M 1/2055; A01M 7/00; A01M 7/005
USPC .............................. 43/132.1, 124, 107, 1, 131
See application file for complete search history.

(56) References Cited

U.S. PATENT DOCUMENTS

| | | | |
|---|---|---|---|
| 1,831,476 A * | 11/1931 | Bennett | 43/124 |
| 2,109,642 A * | 3/1938 | Hunt | 43/124 |
| 3,234,083 A * | 2/1966 | Hardy et al. | 514/729 |
| 3,501,472 A * | 3/1970 | Horne et al. | 544/408 |
| 3,590,119 A * | 6/1971 | Cardarelli | 43/131 |
| 3,855,313 A * | 12/1974 | Metcalf et al. | 568/56 |
| 3,906,103 A * | 9/1975 | Kushlefsky et al. | 514/493 |
| 3,939,277 A * | 2/1976 | Metcalf et al. | 514/717 |
| 3,997,999 A * | 12/1976 | Evans | 43/107 |
| 4,009,259 A * | 2/1977 | Ament et al. | 424/184.1 |
| 4,112,946 A * | 9/1978 | Herschler | 604/290 |
| 4,166,112 A * | 8/1979 | Goldberg | 424/93.461 |
| 4,206,281 A * | 6/1980 | Goldberg | 435/30 |
| 4,218,843 A * | 8/1980 | Clarke, Jr. | 43/131 |
| 4,228,614 A * | 10/1980 | Cardarelli | 43/131 |
| 4,328,636 A * | 5/1982 | Johnson | 43/107 |
| 4,333,922 A * | 6/1982 | Herschler | 424/184.1 |
| 4,631,857 A * | 12/1986 | Kase et al. | 43/132.1 |
| RE32,356 E * | 2/1987 | Cardarelli | 514/89 |
| 4,732,762 A * | 3/1988 | Sjogren | 424/409 |
| 5,194,264 A * | 3/1993 | Van Tonder | 424/405 |
| 5,273,967 A * | 12/1993 | Pittendrigh | 424/93.461 |
| 5,389,257 A * | 2/1995 | Todd et al. | 210/602 |
| 5,484,600 A * | 1/1996 | Sjogren | 424/405 |
| 5,665,555 A * | 9/1997 | Sweeney et al. | 435/7.21 |
| 5,720,329 A * | 2/1998 | Clarke, Jr. | 43/132.1 |
| 5,792,750 A * | 8/1998 | Borovsky et al. | 514/1.3 |
| 5,983,557 A * | 11/1999 | Perich et al. | 43/132.1 |
| 6,185,861 B1 * | 2/2001 | Perich et al. | 43/132.1 |
| 6,303,364 B1 * | 10/2001 | Thompson et al. | 435/252.3 |
| 6,335,027 B1 * | 1/2002 | Levy | 424/409 |
| 6,337,078 B1 * | 1/2002 | Levy | 424/406 |
| 6,346,262 B1 * | 2/2002 | Levy | 424/408 |
| 6,389,740 B2 * | 5/2002 | Perich et al. | 43/132.1 |
| 6,391,201 B1 * | 5/2002 | Pelz | 210/602 |
| 6,603,063 B1 * | 8/2003 | Feitelson et al. | 800/302 |
| 6,662,491 B2 * | 12/2003 | Flinn et al. | 43/132.1 |
| 6,708,443 B2 * | 3/2004 | Hall | 43/132.1 |
| 6,772,694 B1 * | 8/2004 | Pearce et al. | 43/132.1 |
| 6,898,898 B1 * | 5/2005 | Cohen et al. | 43/132.1 |
| 7,094,592 B2 * | 8/2006 | Watanabe et al. | 435/252.5 |
| 7,361,268 B2 * | 4/2008 | Ogden | 210/150 |
| 7,434,351 B2 * | 10/2008 | Bette | 43/131 |
| 7,563,453 B2 * | 7/2009 | Dupree et al. | 424/405 |
| 7,694,455 B1 * | 4/2010 | Bowden et al. | 43/132.1 |
| 7,837,988 B2 * | 11/2010 | Sjogren et al. | 424/93.4 |
| 7,892,571 B2 * | 2/2011 | Sjogren et al. | 424/409 |
| 7,946,077 B2 * | 5/2011 | Fukuhara | 43/132.1 |
| 8,109,035 B2 * | 2/2012 | Bowden et al. | 43/132.1 |
| 8,187,618 B2 * | 5/2012 | Sjogren et al. | 424/409 |
| 8,216,825 B2 * | 7/2012 | Yuan | 435/257.1 |
| 2003/0056427 A1 * | 3/2003 | Daffunchio et al. | 43/124 |
| 2006/0239977 A1 * | 10/2006 | Sjogren et al. | 424/93.4 |
| 2008/0254000 A1 * | 10/2008 | Drahos et al. | 424/93.4 |
| 2011/0151508 A1 * | 6/2011 | Lopez-Cervantes et al. | 435/42 |
| 2011/0158946 A1 * | 6/2011 | Durvasula et al. | 119/212 |
| 2011/0268780 A1 * | 11/2011 | Markus et al. | 424/408 |
| 2012/0064180 A1 * | 3/2012 | Bossier et al. | 424/718 |
| 2012/0284165 A1 * | 11/2012 | Morgenthaler et al. | 705/37 |
| 2012/0315668 A1 * | 12/2012 | Lopez-Cervantes et al. | 435/42 |
| 2013/0276355 A1 * | 10/2013 | Koehler et al. | 43/132.1 |
| 2013/0296370 A1 * | 11/2013 | Di Martino et al. | 514/333 |

FOREIGN PATENT DOCUMENTS

DE           4313109 A1 * 10/1994 ............. G01N 33/18

* cited by examiner

*Primary Examiner* — Darren W Ark
(74) *Attorney, Agent, or Firm* — VLP Law Group LLP; Kent H. Cheng

(57) ABSTRACT

The invention relates to a method for the eradication and killing of microorganisms from among insects and worms in an aqueous system, especially for the control and eradication of the larvae. A sustained reduction or killing of the larvae is achieved by a two-step method in which insecticides and a zooplankton community are used as biological agents. The insecticides specifically kill the larvae present in the aqueous system. The biological agents, which according to the invention preferably comprise competitors for food of the above microorganisms/larvae, prevent repopulation. The combined use of insecticidal and biological treatment in aqueous systems allows an efficient and permanent eradication.

12 Claims, No Drawings

METHOD FOR THE ERADICATION OF PATHOGENIC MICROORGANISMS IN AN AQUEOUS SYSTEM

PRIORITY CLAIM

This is a U.S. national stage of application No. PCT/EP2009/065025, filed on Nov. 12, 2009. Priority is claimed on the following application: German Application No.: 102008043715.8 filed on Nov. 13, 2008, the content of which is incorporated here by reference.

BACKGROUND OF THE INVENTION

The invention relates to a method for the control and destruction of pathogenic microorganisms, in particular insects and worms, in an aquatic system, preferably for monitoring and controlling larvae. In a preferred fashion the invention relates to a method for controlling gnat/mosquito larvae in water bodies. Sustained reduction of microorganisms or destruction of their larvae is achieved by a two-step process in which chemical agents, such as insecticides, and biological agents are used in combination. Chemical agents specifically kill the larvae (e.g. mosquitoes) present in the aquatic system. Recolonization is prevented by zooplankton communities as biological agents which, according to the invention, preferably comprise food competitors of the microorganisms and larvae thereof. The combined use of chemical (insecticidal) and biological treatment in aquatic systems allows efficient and lasting control of insects and worms.

Numerous pathogenic microorganisms from the families of insects and worms are doing damage to humans, animals and plants. More specifically, the threat of insects, preferably mosquitoes, as carriers of disease (vectors) is increasing worldwide. This applies to tropical regions (Epstein, 1998), but also increasingly to temperate climates, for instance, the spread of *Aedes albopictus* in Italy since 1990 and its recent spread towards Germany (Knudsen et al., 1996). The outbreaks of Chikungunya fever in North-East Italy (Enserink, 2008) and the number of West Nile virus cases reported recently in USA and Europe (Balenghien, 2007) demonstrate the increasing relevance of vector-borne diseases to humans. As climate change and associated changes in weather (e.g., warming, rainfall patterns and resulting floods) are expected to continue, the problems associated with insects such as mosquitoes—and the diseases they transmit—are likely to increase in the future. Apart from mosquitoes, the schistosomiasis-causing larvae of schistosomes (trematodes), for example, likewise represent a major problem. There is thus an urgent need to develop effective methods of controlling such populations.

Thus, for example, mosquitoes live in two highly different habitats:
In the water: the eggs are laid here to develop larvae which feed on small organisms (such as algae, bacteria) in the water. The larvae pupate after several days of development. Finally, the adults (adult, winged animals) emerge from the pupae.
In the air and on land: the flying adult individuals hatch from the pupae and live outside the water.

Mosquitoes are typical pioneer species (first species to colonize newly formed water bodies). For this reason, mosquitoes are frequently found in new or periodically drying water bodies, i.e., waters wherein few other species (e.g. those acting as competitors) are encountered.

As a rule, insecticides (chemical toxins) destroying the larvae are used in water bodies to reduce the larvae. The associated problems are well-known:
(1) Rapid recolonization by larvae: a short time after chemical treatment (a few days or a few weeks), new populations of larvae will form after oviposition of surviving insects.
(2) Stress on the ecosystem: chemical treatment may have strong effects on organisms other than insects. As a result, this may disturb the entire ecosystem being treated.
(3) Development of resistant insects: repeated chemical control treatment of populations frequently results in the development of resistance. As a consequence, the chemical effectiveness of control measures is reduced. In response, it is necessary to implement cost-intensive multiple treatments using higher concentrations.

The invention was therefore based on the object of developing a method for the control and destruction of pathogenic and/or troublesome insects and worms, which method no longer has the disadvantages of agents previously used, or only to a minor extent.

SUMMARY OF THE INVENTION

Said object is accomplished by means of a two-step method for the control and destruction of human, animal and plant pathogenic microorganisms from the families of insects and worms and larvae thereof in an aquatic system. The method is used in aquatic systems which contain said insects and worms and/or larvae thereof or tend to allow their growth therein, i.e., in water bodies wherein mosquito eggs may already be present. According to the invention, effective amounts of at least one insecticide and, at the same time, a zooplankton community as biological agent are added to the aquatic system. The insecticide(s) and biological agents are used in a harmonized manner, so that the development of the biological agent would not be impaired or only to a minor extent.

It is preferred to use an effective amount of a chemical and/or bacterial insecticide that has a specific (selective) effect. According to the invention, food competitors of the insects, worms and larvae are preferably used as biological agents. According to the invention, said food competitors are zooplankton communities. In a preferred fashion the agents are placed on the surface of the aquatic system and/or incorporated in the aquatic system at the same time. The inventive combination allows effective and lasting reduction of larvae by using toxins with a specific effect and the above-described process of biological competition in close temporal proximity.

The invention makes use of the finding that the abundance of pioneer species such as mosquitoes decreases in water bodies bearing water for a prolonged period of time, while other species such as *daphnia* and copepods (zooplankton communities) become more abundant. Most of the species gradually replacing the insects are competitors for food, thereby reducing the food resources of these insects. However, the process of reducing larvae cannot be applied in practice because technical operation is ineffective. One major drawback is that displacement of the larvae by competitors is exceedingly slow, so that displacement takes several months.

More specifically, the human, animal and plant pathogenic insects to be controlled are mosquitoes or gnats. Control is understood to be reduction of a population. The method according to the invention is specifically directed to the control of pathogenic insects by destroying the larvae thereof in their preferred habitat, i.e. an aquatic system. Aquatic systems are understood to be water bodies in general, i.e. usually shallow waters, such as banks of lakes, ponds, rice fields, marshes and the like.

Apart from mosquitoes, insects to be controlled according to the invention are flies and bugs that transmit protozoa, nematodes and viruses upon bite or contact and thereby may cause serious diseases.

Pathogenic worms of particular interest in association with disease transmission and thus requiring control include schistosomiasis-causing schistosomes (trematodes, leeches), the larvae of which are present in brackish and fresh water, or fish pathogenic tapeworms and nematodes living in water.

The method of the invention combines the chemical method of control and an ecological component for long-term control of larvae by promoting or incorporating natural competitors.

As mentioned above, the preferred insecticides are used in combination with biological agents representing natural competitors of the insects. Preferred zooplankton communities are mixed or single-species zooplankton communities likewise utilizing the food resources in the area, so that recovery of the larvae is suppressed and prevented. In general, zooplankton is understood to represent animal microorganisms freely floating in sea or fresh water, usually microscopically small animal organisms, including e.g. species such as crustaceans and other invertebrates.

By using insecticides and food competitors in close temporal proximity, the inventive combination results in nearly complete suppression of new larval development.

The applied insecticides reduce the abundance of larvae towards zero. When selecting the insecticide, care should be taken that damage to competitors is as low as possible. According to the invention, it is preferred to select substances having a selective effect which, on the one hand, rapidly destroy in particular the larvae and, on the other hand, do not damage the zooplankton communities and allow rapid growth thereof. Owing to the use of insecticides, larvae and thus rivals for food are barely present anymore. In this way, resurgence of the population after the use of insecticides is prevented as a result of the presence of natural competitors. Application of the insecticide can be as a single use, and additional use is usually not necessary. In this way, the disadvantages of the prior art in using insecticides can be reduced, and the additional use of food competitors for the larvae makes treatment with further toxic substances unnecessary. The success of the method is based on the fact that two components responsible for the development of larvae are affected: short-term reduction of larvae by the insecticides (preferably so-called larvicides) and long-term prevention of recolonization by incorporating zooplankton communities (food competitors).

The inventive method for the control of larvae is far superior to previous methods merely comprising the chemical component, i.e. insecticide treatment, which results in a short-term reduction of larvae. The present method achieves long-lasting suppression of larvae development, which has not been possible with well-known agents and methods. Being a combination of chemical and biological components, the method according to the invention is perfectly suited to effect long-term destruction and/or control of larvae.

The insecticides used as part of the invention for the initial reduction of larvae have a specific effect against the respective population and have no or barely any adverse effects on other species, such as potential competitors and enemies of the larvae. The concentration of the insecticide to be used is selected such that it kills a major proportion of the larvae. That is, more than 70% must be destroyed within the first 4 days following application, and adverse effects on other species should be very small.

In a preferred fashion, chemical and/or bacterial insecticides are used, and single addition thereof should normally be sufficient to destroy the larvae. If necessary, however, application of the insecticide can be repeated. To this end, the insecticide can be placed, preferably sprayed, on the surface of the aquatic system containing the larvae or can be incorporated in the aquatic system and preferably sprayed near the surface. The insecticide can be used in various formulations, e.g. in liquid form, as a floating powder, a floating oil, in the form of solids or emulsions. The insecticides are used at any dosage that allows destruction of a major part (at least 70%) of the human, animal and plant pathogenic microorganisms. In a preferred fashion they are effectively employed at a dosage of about 0.5 to 1.5 l/ha or 0.5 to 1.5 $g/m^3$.

Insecticides having a specific effect are well-known to those skilled in the art. Some agents used according to the invention will be mentioned as representatives herein.

For example, a bacterial insecticide for mosquito larvae that is preferably used is *Bacillus thuringienis israelensis*. *Bacillus thuringienis israelensis* (Bti) is a bacterium, i.e. a microorganism, ingested in particular by mosquito larvae during feeding. For use, Bti in the form of e.g. a powder, a liquid or a tablet simply must be placed in the breeding waters. Bti bacteria contain a special protein crystal that is extremely toxic to larvae. However, this applies to mosquito larvae only. The protein crystal is completely harmless and ultimately ineffective for humans, fish, or even other insects. The first larvae die as early as 15-20 minutes after ingesting the bacteria. The bacterial insecticide for the control of mosquito larvae is preferably used at a dosage of about 0.5 to 1.5 l/ha, preferably 0.8 l/ha.

Other insecticides having a specific effect are e.g. substances from the class of neonicotinoids, all of which are synthetic nicotine compounds, including chloronicotinyl compounds such as imidacloprid, thiacloprid, which have a chloropyridyl heterocycle, or thianicotinyl compounds such as thiamethoxam, clothianidin, which have a chlorothiazol heterocycle.

Treatment with the insecticides produces a system substantially free of larvae. The ecological treatment prevents larvae from recolonizing the habitat. For ecological treatment, a potentially natural community is added to the aquatic system at the same time, i.e. in close temporal proximity. Surprisingly, such addition significantly accelerates the natural succession (development) of the biotic community in the system towards a community including a large number of food competitors and predators of larvae.

A suitable zooplankton community (competitors and predators of the respective larvae to be controlled) can be collected in nearby, long-standing water bodies, i.e. bearing water for a prolonged period of time. In such water bodies the succession has usually progressed to such an extent that competitors and predators of larvae are naturally present. The initial density of the community in the original water is about 10 to 100 individuals per liter. It is also possible to breed competitors and predators of larvae. Following transfer of the organisms into the aquatic system to be treated, the communities of competitors and predators of larvae develop up to high densities within a few days up to two weeks. The rate of development depends on the initial density of organisms employed and the physical and chemical conditions in the water. According to the invention, it is preferred to use a mixed community usually comprising the following species: *Daphnia, Ceriodaphnia, Simocephalus, Scapheloberis,*

*Ostracoda* and/or *Cyclopoida*. A single-species community is understood to represent communities consisting of one single kind of a suitable competitor. Suitable competitors that can be used as single species are, for example, *Daphnia* species that are food competitors of mosquitoes. If necessary, the zooplankton communities can be accumulated by means of water filtration, using e.g. suitable nets, preferably with a mesh size of about 180 µm.

Advantageously, the zooplankton community is incorporated in the water at a dosage that exceeds the amount of human, animal and plant pathogenic microorganisms after pesticide treatment and is e.g. 10 to 200 individuals/liter.

Such ecological treatment, i.e. addition of a community existing in a natural context as well, reduces (i) recolonization of mosquito larvae following chemical insecticide treatment, and (ii) development and survival rate of possibly existing larvae. The mechanisms of this negative influence are, firstly, competition for food and, secondly, the impact of natural enemies of the mosquito larvae.

Particularly successful control of mosquito larvae is achieved by combined treatment of the larvae using Bti and a zooplankton community. The preferred community has the following taxa: *Daphnia, Ceriodaphnia, Simocephalus, Scapheloberis, Ostracoda* and *Cyclopoida*, preferably in proportions of 4, 74, 7, 3, 10 and 1%. Following single application of the insecticide in combination with the zooplankton community, a few mosquito larvae are observed only in some cases even after 3 weeks.

As a result of the development of competitors and predators, the method according to the invention allows successful prevention of recolonization following treatment with insecticides having a specific effect. Lasting suppression of the larvae is achieved unless the water body dries up or some other interference significantly impairs the community of competitors and predators. In addition to studies in Germany (see examples below), the results of investigations in e.g. Cameroon, Africa, demonstrate that the method according to the invention can also be used successfully in other climatic regions (e.g. tropical and subtropical areas).

DETAILED DESCRIPTION OF THE PRESENTLY PREFERRED EMBODIMENTS

Examples

Example 1

The method was examined in its effectiveness using artificial outdoor water bodies (60 liters). The water bodies were colonized by a natural population of *Culex pipiens*. Initial chemical treatment was carried out using the *Bacillus thuringienis israelensis* insecticide (Bti, Vectobac 12S) at 1 g/m³.

In procedure "A" the insecticide was used alone.
In procedure "B" it was only a mixed zooplankton community that was placed in the water bodies (50 individuals/liter).
In procedure "C" the pesticide and a mixed zooplankton community were placed in the water bodies (50 individuals/liter) at the same time.
No manipulation in procedure "D".

If insecticide was used ("A", "C"), the mosquito larvae population decreased from about 200 larvae/liter to 0 larvae per liter within the first two days. If chemical treatment was carried out alone ("A"), the water bodies were recolonized by mosquito larvae within the next 20 days (about 150 larvae/liter). This amount was comparable to the number of larvae in procedure "D" (no treatment). If a combined chemical and biological treatment was used ("C"), no mosquito larvae were present in the water bodies until the end of the test after 20 days. In the purely biological procedure ("B") there was only a gradual reduction in the density of mosquito larvae from 280 individuals/liter down to 50 individuals/liter during the 20 days of testing.

Example 2

The method was applied in natural, newly formed small water bodies in riparian forests in the region of Leipzig, Germany, in summer 2008. The water bodies were colonized by a natural population of *Culex pipiens*. Initial chemical treatment was carried out using the *Bacillus thuringienis israelensis* insecticide (Bti, Vectobac 12S) at 1 g/m³.

In procedure "A" the insecticide was used alone.
In procedure "B" the insecticide and a mixed zooplankton community (*Daphnia, Ceriodaphnia, Simocephalus, Scapheloberis, Ostracoda, Cyclopoida* in proportions of 4, 74, 7, 3, 10 and 1%; a total of about 100 individuals/liter) were placed in the water bodies at the same time.

The results demonstrated that the mosquito larvae decreased within the first three days from about 200 larvae/liter down to 0 larvae/liter in both procedures. In procedure "A" (no community) the water bodies were recolonized by mosquito larvae from day 4 on. About 250 larvae per liter were present after 20 days. In procedure "B" (including community) a few mosquito larvae were observed only in some cases after 20 days.

Both examples show that sustainable and thus effective control of mosquito larvae is only possible by the combined effect of insecticides and competitors and predators of the mosquito larvae.

The invention claimed is:

1. A method for the control and destruction of insects and worms and larvae thereof in an aquatic system which contains said insects, worms and/or larvae, the method comprising adding at least one bacterial insecticide in combination with a zooplankton community to the aquatic system to reduce or kill the insects, worms and/or larvae thereof.

2. The method according to claim 1, wherein the at least one bacterial insecticide is *Bacillus thuringienis israelensis*.

3. The method according to claim 1 wherein the at least one bacterial insecticide is used at a dosage of from 0.5 to 1.5 l/ha or from 0.5 to 1.5 g/m³.

4. The method according to claim 1, wherein the at least one bacterial insecticide is used in liquid form, in the form of floating powders, oils, as solids or in emulsions.

5. The method according to claim 1, wherein the at least one bacterial insecticide is placed on a surface of the aquatic system or incorporated in the aquatic system, by spraying near the surface.

6. The method according to claim 1, wherein the zooplankton community is a mixed or single-species zooplankton community taken from water bodies or bred which are incorporated as the zooplankton community in the aquatic system.

7. The method according to claim 1, wherein the zooplankton community comprises the *Daphnia, Ceriodaphnia, Simocephalus, Scapheloberis, Ostracoda* and/or *Cyclopoida* taxa.

8. The method according to claim 1, wherein the zooplankton community is incorporated in the water bodies at a dosage of from 10 to 200 individuals/l.

9. The method according to claim 1, wherein the at least one bacterial insecticide which comprises *Bacillus thuringienis israelensis* is used in combination with the zooplankton community which comprises *Daphnia, Ceriodaphnia, Simocephalus, Scapheloberis, Ostracoda* and *Cyclopida.*

10. The method according to claim 9, wherein the at least one bacterial insecticide which comprises *Bacillus thuringienis israelensis* is used at an effective dosage of about 0.5 to 1.5 g/m$^3$ in combination with the zooplankton community which comprises *Daphnia, Ceriodaphnia, Simocephalus, Scapheloberis, Ostracoda*, and *Cyclopida* in proportions of 4, 74, 7, 3, 10 and 1% and has a sufficient amount of competitors, about 10 to 200 individuals/liter.

11. The method according to claim 10, wherein the at least one bacterial insecticide does not impair the development of the zooplankton community, and said method is used to reduce or kill mosquito and gnat larvae in an aquatic system.

12. The method according to claim 1, wherein the at least one bacterial insecticide and the zooplankton community are added to the aquatic system simultaneously or in close temporal proximity, said insecticide being applied once or several times.

\* \* \* \* \*